(12) United States Patent
Cefalo et al.

(10) Patent No.: US 7,087,755 B1
(45) Date of Patent: Aug. 8, 2006

(54) SUBSTITUTED PYRIDINES

(75) Inventors: Dustin R. Cefalo, Hyrum, UT (US); Jason I. Henderson, River Heights, UT (US); Homayoun H. Mokri, North Logan, UT (US)

(73) Assignee: Frontier Scientific, Inc., Logan, UT (US)

( * ) Notice: Subject to any disclaimer, the term of this patent is extended or adjusted under 35 U.S.C. 154(b) by 0 days.

(21) Appl. No.: 11/272,215

(22) Filed: Nov. 10, 2005

Related U.S. Application Data

(60) Provisional application No. 60/626,943, filed on Nov. 12, 2004.

(51) Int. Cl.
 *C07D 213/04* (2006.01)
 *C07D 213/60* (2006.01)

(52) U.S. Cl. ............................................. 546/13; 546/1

(58) Field of Classification Search .................. 546/13, 546/1
 See application file for complete search history.

(56) References Cited

FOREIGN PATENT DOCUMENTS

WO  WO 02/078701  * 10/2002

OTHER PUBLICATIONS

Parry, P. et al.: New Shelf-stable halo- and alkoxy-substituted Pyridylboronic acids and their Suzuki cross-coupling reactions to yield heteroarylpyridines. Synthesis, No. 7, pp. 1035-1038, 2003.*

Parry, P. et al.: Functionalized pyridylboronic acids and their Suzuki cross-coupling reactions to yield novel heteroarylpyridines. J. Org. Chem. vol. 67, pp. 7541-7543, 2002.*

Abo-Amer, A. et al.: Polyfluoroorganotrifluoroborates and difluoroboranes: interesting materials in fluoroorgano and fluoroorgano-element chemistry. J. of Fluorine Chem. vol. 125, pp. 1771-1778, 2004.*

Alexandre Bouillon et al, "Synthesis of novel halopyridinylboronic acids and esters," Tetrahedron 58 (2002) 4369-4373.

M. Schlosser et. al., "Regiochemically Flexible Substitutions of Di-, Tri-, and Tetrahalopyridines: The Trialkylsilyl Trick," J. Org. Chem., 2005, 70, 2494-2502.

Queguiner et al, "A New Convergent Route to 1-Substituted Ellipticines," J. Org. Chem. 1992, 57, 565-573.

* cited by examiner

*Primary Examiner*—Charanjit S. Aulakh
(74) *Attorney, Agent, or Firm*—Alvin T. Rockhill

(57) ABSTRACT

A class of 2,4-; 2,3,4-; 2,4,6-; 2,3,4,5,6-substituted pyridines is provided which include novel compounds. The substitutions are achieved according to methods disclosed herein in which a metallated pyridine is reacted with an electrophile. Suitable electrophiles include $CO_2$, $SO_2$, dialkylcarbonates, ureas, formamides, amides, carboxylic acid esters, mono- and dihaloalkyls, halogens such as chlorine, fluorine, bromine, and iodine, metallic salts, sulfones, sulfonyls, aldehydes, ketones, anhydrides, nitrites, and electrophilic boron compounds including, but not limited to, boron trialkoxides and boron trihalides. The subject invention more specifically discloses a process for the synthesis of 2,6-difluoropyridin-4-ylboronic acid which comprises: (1) reacting 2,4,6-trifluoropyridine with hydrazine monohydrate to produce 2,6-difluoro-4-hydrazinopyridine, (2) reacting the 2,6-difluoro-4-hydrazinopyridine with elemental bromine to produce 4-bromo-2,6-difluoropyridine, and (3) reacting the 4-bromo-2,6-difluoropyridine with an organolithium compound and a borate at a temperature of less than about 0° C. to produce the 2,6-difluoropyridin-4-ylboronic acid, wherein said process is conducted in an organic solvent.

25 Claims, No Drawings

SUBSTITUTED PYRIDINES

This application claims the benefit of U.S. Provisional Patent Application Ser. No. 60/626,943 filed on Nov. 12, 2004.

BACKGROUND OF THE INVENTION

The present invention relates to substituted pyridines and synthetic methods for producing the same. More specifically, the present invention provides a family of 2,4-; 2,3,4-; 2,4,6-; 2,3,4,6-; 2,3,4,5,6-substitued pyridines using novel methods disclosed herein.

SUMMARY OF THE INVENTION

The present invention provides novel 2,4-; 2,3,4-; 2,4,6; 2,3,4,6-; 2,3,4,5,6-substituted pyridines and methods for their synthesis. More specifically, the present invention provides a family of 2,4-; 2,3,4-; 2,4,6; 2,3,4,6-; 2,3,4,5,6-substituted pyridines and specific 2-substituted pyridine-4-boronic acids created by reacting a metallated pyridine with an electrophile. Suitable electrophiles include, but are not limited to, $CO_2$, $SO_2$, dialkylcarbonates, ureas, formamides, amides, carboxylic acid esters, haloalkyls, dihaloalkyls, halogens (such as, but not limited to, chlorine, fluorine, bromine, and iodine), metallic salts, sulfones, sulfonyls, aldehydes, ketones, anhydrides, nitriles, and electrophilic boron compounds including, but not limited to, boron trialkoxides and boron trihalides. These novel molecules are produced using novel methods also disclosed herein.

Accordingly, the present invention provides a family of di-, tri-, tetra- and pentasubstituted pyridines having the general formula:

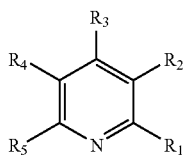

According to the present invention $R_1$, $R_2$, $R_3$, $R_4$ and $R_5$ may be substitutions produced by reacting a metallated pyridine with an electrophile. Suitable electrophiles include, but are not limited to, $CO_2$, $SO_2$, a wide variety of dialkylcarbonates, ureas, formamides, amides, carboxylic acid esters, mono- and dihaloalkyls, halogens (such as, but not limited to, chlorine, fluorine, bromine, and iodine), metallic salts, sulfones, sulfonyls, aldehydes, ketones, anhydrides, nitriles, and electrophilic boron compounds including, but not limited to, boron trialkoxides and boron trihalides according to the methods described herein.

The substituted pyridines of the invention are produced using the methods of the invention outlined herein, and may be adapted to provide a wide variety of substitution patterns, including 2,4-disubstituted pyridines, 2,3,4-trisubstituted pyridines, 2,4,6-trisubstituted pyridines, 2,3,4,6-tetrasubstituted pyridines, and 2,3,4,5,6-pentasubstituted pyridines. Some substituted pyridines and methods of their syntheses are specifically taught within the scope of this invention. The methods taught for the synthesis of these compounds may be adapted by those of ordinary skill in the art to provide for substitutions at the 2, 3, 4, 5 and 6 positions. Further, the methods of the invention may be modified to create the various substitutions in different position, i.e., using existing substitution direct metallation at adjacent positions followed by reacting with an electrophile to create substitution that can be used to direct metallation at another adjacent position, by one of skill in the art.

The present invention more specifically discloses a pyridine compound of the structural formula:

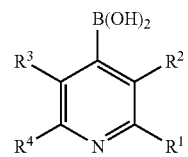

wherein $R^1$ is a moiety selected from the group consisting of halogen atoms, —$NH_2$ groups, —NHBOC groups, —CN groups, —COOH groups, —CHO groups, and —O—$(CH_2)_nCH_3$ groups, wherein $R^2$, $R^3$, and $R^4$ can be the same or different and are selected from the group consisting of hydrogen atoms, halogen atoms, —$NH_2$ groups, —NHBOC groups, —CN groups, —COOH groups, —CHO groups, and —O—$(CH_2)_nCH_3$ groups, with the proviso that if $R^1$ is a halogen atom then R or $R^4$ is a moiety other than a hydrogen atom.

The subject invention also discloses a process for the synthesis of 2,6-difluoropyridin-4-ylboronic acid which comprises: (1) reacting 2,4,6-trifluoropyridine with hydrazine monohydrate to produce 2,6-difluoro-4-hydrazinopyridine, (2) reacting the 2,6-difluoro-4-hydrazinopyridine with elemental bromine to produce 4-bromo-2,6-difluoropyridine, and (3) reacting the 4-bromo-2,6-difluoropyridine with an organolithium compound and a borate at a temperature of less than about 0° C. to produce the 2,6-difluoropyridin-4-ylboronic acid, wherein said process is conducted in an organic solvent.

DETAILED DESCRIPTION OF THE INVENTION

The functionalized pyridinylboronic acids of this invention are useful in combinatorial approaches by virtue of their boronic moiety and at least one additional functional group. These substituted pyridinylboronic acids are a value in pharmacological discovery research applications and are typically of the structural formula:

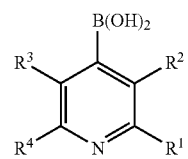

wherein $R^1$ is a an orthometallating group, wherein $R^2$, $R^3$, and $R^4$ can be the same or different and are selected from the group consisting of hydrogen atoms and orthometallating groups, with the proviso that if $R^1$ is a halogen atom then $R^2$ or $R^4$ is a moiety other than a hydrogen atom.

The pyridinylboronic acids can for instance be substituted with a primary, secondary, or tertiary amine such as shown in the formula:

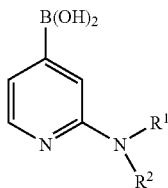

and

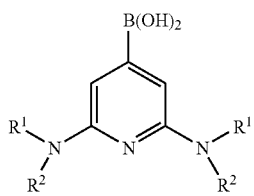

wherein $R^1$ nand $R^2$ can be the same or different and are selected from the group consisting of hydrogen atoms, alkyl groups containing from 1 to 10 carbon atoms, and arene moieties containing from 1 to 10 carbon atoms. For purposes of this invention arene moieties are groups that contain both aliphatic and aromatic units. In such compounds $R^1$ and $R^2$ will typically both be hydrogen atoms.

The pyridinylboronic acids can also be substituted with primary, secondary, or tertiary amine such as shown in the formula:

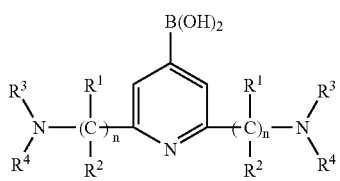

wherein $R^1$, $R^2$, $R^3$, and $R^2$ can be the same or different and are selected from the group consisting of hydrogen atoms, alkyl groups containing from 1 to 10 carbon atoms, and arene moieties containing from 1 to 10 carbon atoms, and wherein n represents an integer from 0 to 10.

The substituted pyridinylboronic acid can also contain an ether moiety as shown in the formulas:

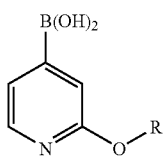

and

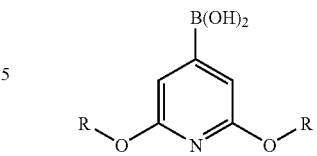

wherein R is selected from the group consisting of alkyl groups containing from 1 to 10 carbon atoms and arene moieties containing from 1 to 10 carbon atoms. In such compounds R will typically represent an alkyl group containing from 1 to 4 carbon atoms, such as a methyl or ethyl group.

The substituted pyridinylboronic acid can be functionalized with a carboxylic acid group or an ester containing group as depicted in the formulas:

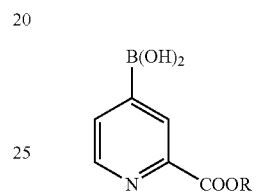

and

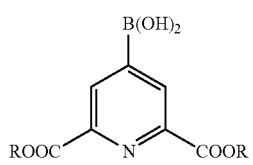

wherein R represents a hydrogen atom, an alkyl groups containing from 1 to 10 carbon atoms, or arene moietiy containing from 1 to 10 carbon atoms.

The pyridinylboronic acid can be substituted with an aldehyde or a ketone containing moiety as depicted in the formulas:

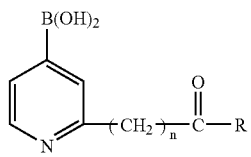

and

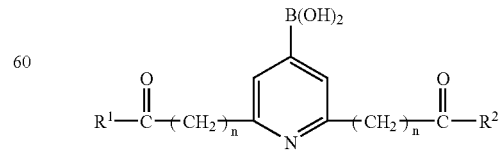

wherein R represents a hydrogen atom, an alkyl group containing from 1 to 10 carbon atoms, or an arene moiety containing from 1 to 10 carbon atoms, wherein $R^1$ and $R^2$ can be the same or different and represents a hydrogen atom, an alkyl group containing from 1 to 10 carbon atoms, or an arene moiety containing from 1 to 10 carbon atoms, and wherein n represents an integer from 1 to 10.

The substituted pyridinylboronic acid can also be substituted with both a halide and an aldehyde or ketone containing moiety as depicted in the formulas:

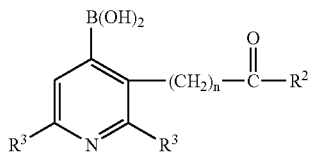

and

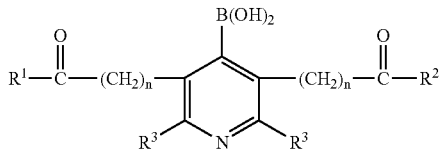

wherein R represents a hydrogen atom or an alkyl group containing from 1 to 10 carbon atoms, wherein $R^1$ and $R^2$ can be the same or different and represents a hydrogen atom, an alkyl group containing from 1 to 10 carbon atoms, or a alkyl group containing from 1 to 10 carbon atoms, wherein $R^3$ represents an orthometallating group, and wherein n represents an integer from 1 to 10.

The substituted pyridinylboronic acids of this invention include those having the specific structural formulas:

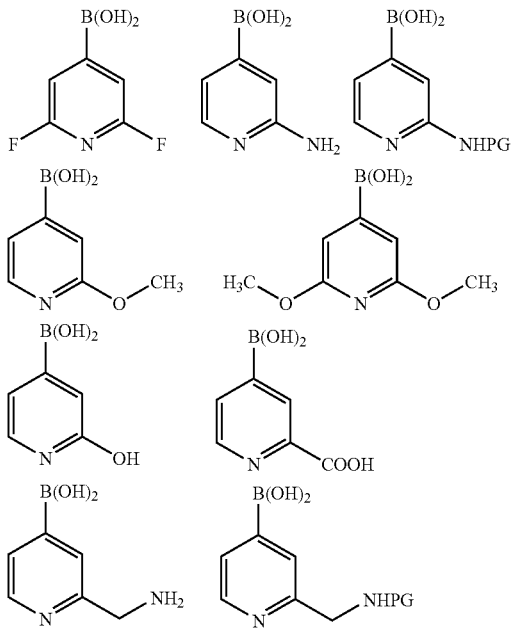

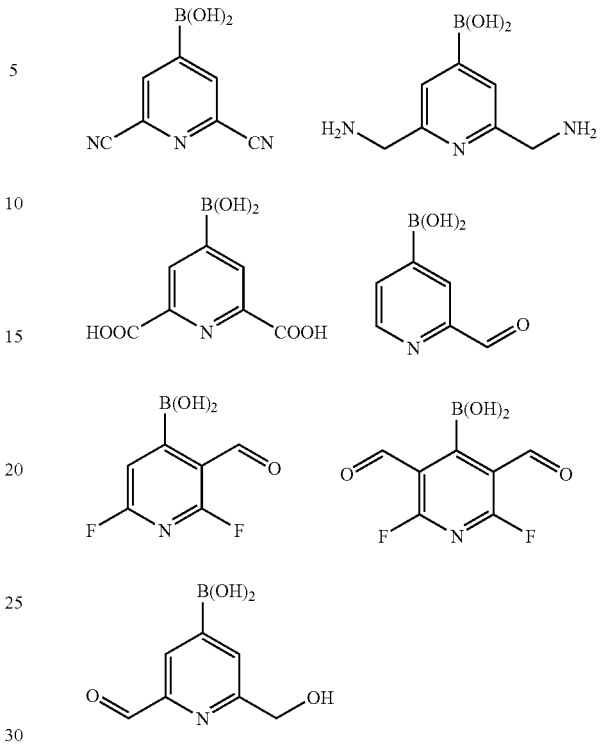

The substituted pyridine compounds of this invention can be made by at least one of two methods. For example, in one of these methods 2,6-difluoropyridin-4-ylboronic acid can be synthesized by a process which comprises: (1) reacting 2,4,6-trifluoropyridine with hydrazine monohydrate to produce 2,6-difluoro-4-hydrazinopyridine, (2) reacting the 2,6-difluoro-4-hydrazinopyridine with elemental bromine to produce 4-bromo-2,6-difluoropyridine, and (3) reacting the 4-bromo-2,6-difluoropyridine with an organolithium compound and a borate at a temperature of less than about 0° C. to produce the 2,6-difluoropyridin-4-ylboronic acid, wherein said process is conducted in an organic solvent. The organic solvent will preferably be a coordinating organic solvent, such as an ether. For instance cyclic ethers such as dioxane, furan, and tetrahydrofuran can be used. This process is typically conducted in tetrahydrofuran (THF). Step (1) is normally conducted at a temperature which is within the range of 0° C. to 100° C., step (2) is normally conducted at a temperature which is within the range of 0° C. to 100° C., and step (3) is normally conducted at a temperature which is within the range of —100° C. to 0° C. Step (1) and step (2) are preferably conducted at a temperature which is within the range of about 20° C. to about 70° C. and step (3) is preferable conducted at a temperature which is within the range of –90° C. to –60° C. It is typically most preferred for step (3) to be conducted at a temperature which is within the range of –80° C. to –70° C. The organolithium compound will generally be an alkyl lithium or a aryl lithium compound that contains from 1 to about 10 carbon atoms. The organolithium compound will typically be an alkyl lithium compound that contains from 1 to about 6 carbon atoms, such as n-propyl lithium, isopropyl lithium, or n-butyl lithium. The borate will typically be a trialkyl borate, a triaryl borate, or a boron trihalide. Such trialkyl borates and triaryl borates will typically contain from 1 to about 8 carbon atoms with triisopropyl borate being a preferred trialkyl borate.

The following examples and the presently preferred embodiments of the present invention will be best understood by reference to the examples that follow. The following examples provide a more detailed description of some of the 2,4-disubstituted pyridines and associated synthetic methods of the present invention. These examples are not intended to limit the scope of the invention or the manner by which it can be practiced and are merely representative of some embodiments of the invention. More specifically, the methods of the invention may be adapted to produce 2,4-; 2,3,4-; 2,4,6-; 2,3,4,6-; and 2,3,4,5,6-substituted pyridines by those skilled in the art and the order of the substitution steps may be altered and still be within the scope of the invention of this invention (see for example, March, Advanced Organic Chemistry, Reactions, Mechanisms, and Structures, 5th Ed., 2001).

This invention is illustrated by the following examples that are merely for the purpose of illustration and are not to be regarded as limiting the scope of the invention or the manner in which it can be practiced. Unless specifically indicated otherwise, parts and percentages are given by weight.

EXAMPLE 1

(Synthesis of 2,6-Difluoropyridin-4-ylboronic acid)

The first step for the production of 2,6-Difluoropyridin-4-ylboronic acid involves the synthesis of 2,6-Difluoro-4-hydrazinopyridine from 2,4,6-trifluoropyridine as described by M. Schlosser. et. al. in J. Org. Chem., 2005, 70, 2494–2502 which is illustrated as follows:

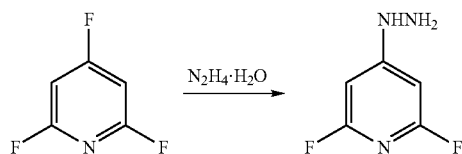

In the first step of this method 2,4,6-trifluoropyridine (100 g, 0.75 mol) and hydrazine monohydrate (75.2 g, 1.5 mol) were heated to 50° C. in tetrahydrofuran (700 ml) for 2 hours. Tetrahydrofuran was removed under reduced pressure and the residue was taken up in water (375 ml) and hexanes (180 ml). After being well mixed with a mechanical stirrer for 15 minutes, the white solids were filtered off and rinsed with 300 ml of cold hexanes.

The material was purified by stirring in refluxing ethyl acetate (600 ml) for 30 minutes. After cooling to room temperature first and then in an ice bath to 0° C., hexanes (400 ml) were added to the ethyl acetate phase and the white solids were filtered off, rinsed with 300 ml of cold hexanes and dried (68 g, 62% yield).

The second step in the synthetic procedure used in synthesizing the 2,6-difluoropyridin-4-ylboronic acid involves bromination of 2,6-difluoro-4-hydrazinopyridine by elemental bromine to produce 4-bromo-2,6-difluoropyridine. This reaction can be depicted as follows:

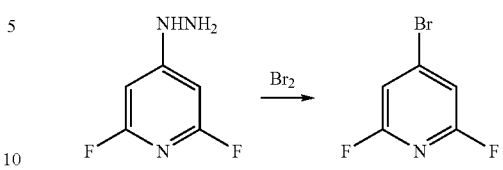

In the second step the reaction flask was charged with 2,6-difluoro-4-hydrazinopyridine (68 g, 0.47 mol) and chloroform (500 ml). Bromine (150 g, 0.93 mol) in 100 ml of chloroform was then added in a slow stream through an addition funnel. Upon completion of addition the addition funnel was replaced with an efficient condenser immediately since the reaction mixture exothermed to 50° C. gradually. The reaction mixture was then heated to reflux for 6 hours, cooled to room temperature and filtered. The filtrate was washed with a saturated solution of sodium thiosulfate (2×250 ml), saturated sodium bicarbonate (1×250 ml, to pH=7), brine (1×250 ml), dried over magnesium sulfate, filtered and concentrated under reduced pressure to a red oil. Distillation provided 44 g of a clear, almost colorless oil.

The third and final step for the production of 2,6-difluoropyridin-4-ylboronic acid involves the lithiation of 2,6-difluoro-4-hydrazinopyridine followed by addition of triisopropyl borate which can be depicted as follows:

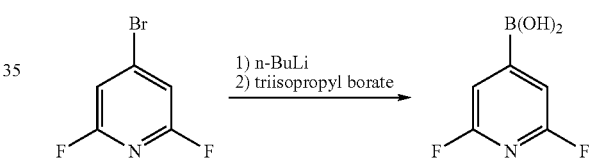

In the final step the reaction flask was charged with tetrahydrofuran (150 ml) and toluene(400 ml). Triisopropyl borate (47 g, 0.25 mol) and 4-bromo-2,6-difluoropyridine (44 g, 0.22 mol) were introduced to the reaction vessel and the mixture was cooled to −75° C. under nitrogen atmosphere. n-BuLi (2.6 M solution in hexanes, 105 ml, 0.27 mol) was added dropwise through an addition funnel, keeping the temperature no higher than 70° C. during the addition process. Upon completion of addition stirring continued at −75° C. for 30 minutes and the cooling bath was removed, allowing the reaction mixture to warm up to −20° C. After quenching with 2 N hydrochloric acid (about 120 ml, to pH=2) and stirring for 30 minutes the organic phase was separated. The aqueous layer was extracted with 250 ml of ether two times. The combined organic phases were then washed with 500 ml of water, 250 ml of brine, dried over magnesium sulfate, stirred with activated charcoal for one hour, filtered through Celite and concentrated under reduced pressure. Hexanes (250 ml) were added to the residue to precipitate the solids. The flask was kept under refrigeration over night and the solids content was collected, rinsed with cold hexanes and dried. Since $^1$H NMR showed the presence of some butyl boronic acid as contaminant, the solids were stirred with hexanes (250 ml) at 45° C. for 30 minutes, filtered while still warm and rinsed with cold hexanes to obtain 11.8 g (33% of the desired product. $^1$H NMR (DMSO) 400 MHz, δ7.31 (s, 2H).

EXAMPLE 2

(Synthesis of 2-fluoropyridine-4-boronic acid)

The first step of the procedure used in this experiment for producing 2-fluoropyridine-4-boronic acid was the synthesis of 3-bromo-2-fluoropyridine, is illustrated by the reaction:

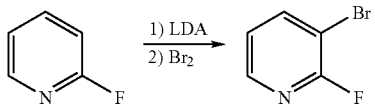

One procedure for carrying out this synthesis is described by Queguiner et. al. in *J. Org. Chem.* 1992, 565–573. Other suitable synthetic methods for preparing this initial compound are known to persons having ordinary skill in the art.

As has previously been discussed, in this step a wide variety of electrophiles may be used in place of bromine. For instance, other suitable electrophiles can be used. Such electrophiles include, but not limited to $CO_2$, $SO_2$, a wide variety of dialkylcarbonates, ureas, formamides, amides, carboxylic acid esters, mono- and dihaloalkyls, halogens (such as, but not limited to, chlorine, fluorine, bromine, and iodine), metallic salts, sulfones, sulfonyls, aldehydes, ketones, anhydrides, nitrites, and electrophilic boron compounds including, but not limited to, boron trialkoxides and boron trihalides (see, March, Advanced Organic Chemistry, Reactions, Mechanisms, and Structures, $5^{th}$ Ed., 2001, the teachings of which are incorporated herein by reference in their entirety).

In the procedure used, 2-fluoropyridine (10 g, 1.03 mol) was dissolved in 2000 mL of tetrahydrofuran. The solution was cooled to −78° C. and a 1.8M solution of lithium diisopropylamide (525 mL, 0.95 mol) was added dropwise into the mixture as it was stirred. The mixture was maintained at −75° C. for 4 hours with the stirring being continued. Bromine (50 mL, 0.98 mol) was slowly added to the stirring mixture ensuring that the mixture was kept below −60° C. The mixture was stirred for 12 more hours at a temperature of −70° C. and then 500 ml of water was added. Then the solution was diluted with an additional 2000 ml of water and 2000 ml of ether. The aqueous and organic layers were then separated. The organic layer was concentrated to afford a dark oil that was purified by distillation under high vacuum to yield 180 grams of a colorless oil. The oil was examined by gas chromatography and was shown to be the desired product which was contaminated with 4-bromo-2-fluoropyridine and ethylbenzene. This mixture was not purified further and was used as obtained from the distillation.

The second step of the production of the 2-fluoropyridine-4-boronic acid utilized in this experiment was the synthesis of 4-bromo-2-fluoropyridine from the 3-bromo-2-fluoropyridine made in the first step. The reaction of this step can be depicted as follows:

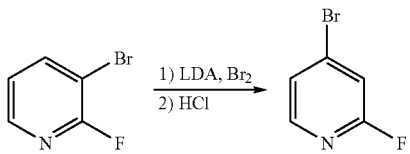

One procedure for carrying out this synthesis is described by Queguiner et. al. in *J. Org. Chem.* 1992, 565–573.

In this step of the synthesis, a wide variety of electrophiles may be used in place of hydrochloric acid actually used in this experimental procedure. Other suitable electrophiles include, but are not limited to $CO_2$, $SO_2$, a wide variety of dialkylcarbonates, ureas, formamides, amides, carboxylic acid esters, mono- and dihaloalkyls, halogens (such as, but not limited to, chlorine, fluorine, bromine, and iodine), metallic salts, sulfones, sulfonyls, aldehydes, ketones, anhydrides, nitrites, and electrophilic boron compounds including, but not limited to, boron trialkoxides and boron trihalides (see, March, Advanced Organic Chemistry, Reactions, Mechanisms, and Structures, $5^{th}$ Ed., 2001, the teachings of which are incorporated herein by reference in their entirety).

The reaction carried out in the third step of the synthesis of the 2-fluoropyridine-4-boronic acid utilized in this experimental procedure can be depicted as follows:

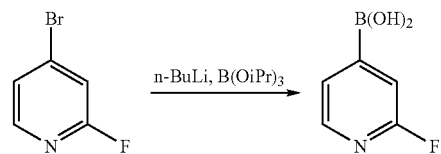

In this step of the synthesis process, a wide variety of electrophiles can again be used in place of triisopropylborate, $B(OiPr)_3$, actually used in this experimental procedure. For instance other suitable electrophiles including, but not limited to $CO_2$, $SO_2$, a wide variety of dialkylcarbonates, ureas, formamides, amides, carboxylic acid esters, mono- and dihaloalkyls, halogens (such as, but not limited to, chlorine, fluorine, bromine, and iodine), metallic salts, sulfones, sulfonyls, aldehydes, ketones, anhydrides, nitrites, and electrophilic boron compounds including, but not limited to, boron trialkoxides and boron trihalides (see, March, Advanced Organic Chemistry, Reactions, Mechanisms, and Structures, $5^{th}$ Ed., 2001, the teachings of which are incorporated herein by reference in their entirety.

While certain representative embodiments and details have been shown for the purpose of illustrating the subject invention, it will be apparent to those skilled in this art that various changes and modifications can be made therein without departing from the scope of the subject invention.

What is claimed is:

1. A functionalized pyridine compound of the structural formula:

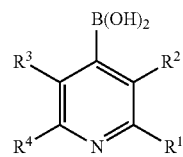

wherein $R^1$ is a moiety selected from the group consisting of halogen atoms, amine groups, —NHBOC, —CN, —COOH, —COOR, —NHPG, CH2NHPG, —$(CH_2)_n$—C(O)R, —CHO, and —OR, wherein $R^2$, $R^3$, and $R^4$ can be the same or different and are selected from the group consisting of hydrogen atoms, NH2, —NHBOC, —CN, —COOH, and —CHO, and wherein R represents alkyl groups containing from 1 to 10 carbon atoms or arene moieties containing from 1 to 10 carbon atoms, wherein PG represents a protecting group, and wherein n represents an integer from 0 to 10, with the proviso that if $R^1$ is a halogen atom then $R^2$ or $R^4$ is a moiety other than a hydrogen atom.

2. A functionalized pyridine compound as specified in claim 1 wherein the functionalized pyridine compound is of the formula:

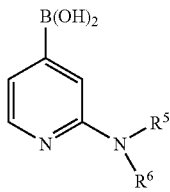

wherein $R^5$ and $R^6$ can be the same or different and are selected from the group consisting of hydrogen atoms, alkyl groups containing from 1 to 10 carbon atoms, and arene moieties containing from 1 to 10 carbon atoms.

3. A functionalized pyridine compound as specified in claim 1 wherein the functionalized pyridine compound is of the formula:

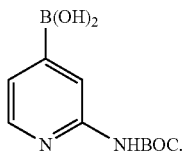

4. A functionalized pyridine compound as specified in claim 1 wherein the functionalized pyridine compound is of the formula:

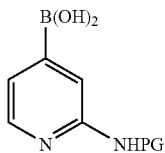

wherein PG represents a protecting group.

5. A functionalized pyridine compound as specified in claim 1 wherein the functionalized pyridine compound is of the formula:

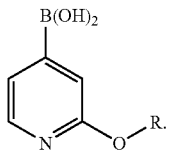

6. A functionalized pyridine compound of the formula:

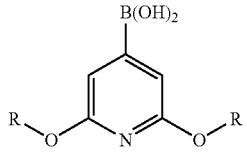

wherein R is selected from the group consisting of alkyl groups containing from 1 to 10 carbon atoms and arene moieties containing from 1 to 10 carbon atoms.

7. A functionalized pyridine compound of the formula:

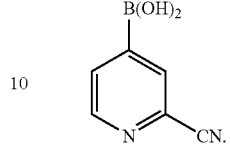

8. A functionalized pyridine compound of the formula:

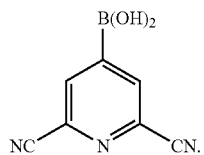

9. A functionalized pyridine compound of the formula:

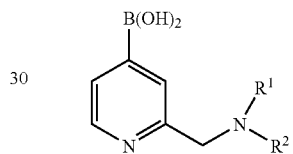

wherein $R^1$ and $R^2$ can be the same or different and are selected from the group consisting of hydrogen atoms, alkyl groups containing from 1 to 10 carbon atoms, and arene moieties containing from 1 to 10 carbon atoms.

10. A functionalized pyridine compound as specified in claim 1 wherein the functionalized pyridine compound is of the formula:

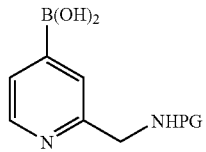

wherein PG represents a protecting group.

11. A functionalized pyridine compound as specified in claim 1 wherein the functionalized pyridine compound is of the formula:

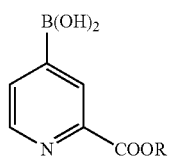

wherein R represents a hydrogen atom, an alkyl groups containing from 1 to 10 carbon atoms, or arene moietiy containing from 1 to 10 carbon atoms.

12. A functionalized pyridine compound of the formula:

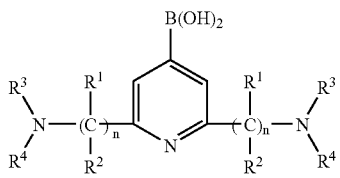

wherein $R^1$, $R^2$, $R^3$, and $R^4$ can be the same or different and are selected from the group consisting of hydrogen atoms, alkyl groups containing from 1 to 10 carbon atoms, and arene moieties containing from 1 to 10 carbon atoms, and wherein n represents an integer from 0 to 10.

13. A functionalized pyridine compound as specified in claim 1 wherein the functionalized pyridine compound is of the formula:

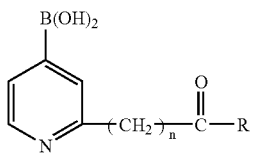

wherein R represents a hydrogen atom, an alkyl group containing from 1 to 10 carbon atoms, or an arene moiety containing from 1 to 10 carbon atoms, and wherein n represents an integer from 0 to 10.

14. A functionalized pyridine compound of the formula:

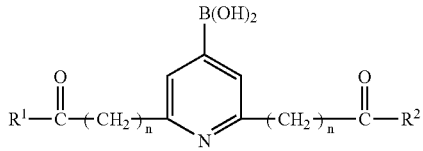

wherein $R^1$ and $R^2$ can be the same or different and represents a hydrogen atom, an alkyl group containing from 1 to 10 carbon atoms, or an arene moiety containing from 1 to 10 carbon atoms, and wherein n represents an integer from 1 to 10.

15. A functionalized pyridine compound of the formula:

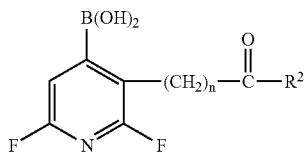

wherein $R^2$ represents a hydrogen atom or an alkyl group containing from 1 to 10 carbon atoms, and wherein n represents an integer from 0 to 10.

16. A functionalized pyridine compound of the formula:

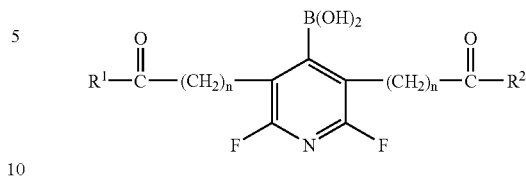

wherein $R^1$ and $R^2$ can be the same or different and represents a hydrogen atom, an alkyl group containing from 1 to 10 carbon atoms, or a alkyl group containing from 1 to 10 carbon atoms, and wherein n represents an integer from 1 to 10.

17. A functionalized pyridine compound as specified in claim 1 wherein the functionalized pyridine compound is of the formula:

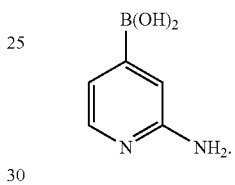

18. A functionalized pyridine compound as specified in claim 1 wherein the functionalized pyridine compound is of the formula:

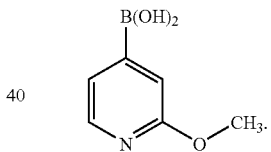

19. A functionalized pyridine compound as specified in claim 1 wherein the functionalized pyridine compound is of the formula:

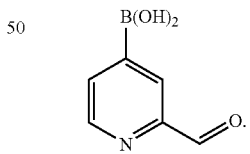

20. A process for the synthesis of 2,6-difluoropyridin-4-ylboronici acid which comprises: (1) reacting 2,4,6-trifluoropyridine with hydrazine monohydrate to produce 2,6-difluoro-4-hydrazinopyridine, (2) reacting the 2,6-difluoro-4-hydrazinopyridine with elemental bromine to produce 4-bromo-2,6-difluoropyridine, and (3) reacting the 4-bromo-2,6-difluoropyridine with an organolithium compound and a borate at a temperature of less than about 0° C. to produce the 2,6-difluoropyridin-4-ylboronic acid, wherein said process is conducted in an organic solvent.

21. A process as specified in claim 20 wherein the solvent is a coordinating organic solvent.

22. A process as specified in claim 21 wherein the coordinating organic solvent is an ether.

23. A process as specified in claim 20 wherein the solvent is tetrahydrofuran.

24. A process as specified in claim 20 wherein step (1) is conducted at a temperature which is within the range of 0° C. to 100° C., wherein step (2) is conducted at a temperature which is within the range of 0° C. to 100° C., and wherein step (3) is conducted at a temperature which is within the range of −90° C. to −60° C.

25. A process as specified in claim 20 wherein the organo lithium compound is n-butyl lithium and wherein the borate is triisopropyl borate.

* * * * *